(12) United States Patent
Liu et al.

(10) Patent No.: US 9,199,199 B2
(45) Date of Patent: Dec. 1, 2015

(54) SEPARATION MEMBRANE

(71) Applicant: UOP LLC, Des Plaines, IL (US)

(72) Inventors: Chunqing Liu, Arlington Heights, IL (US); Gregory F. Maher, Aurora, IL (US)

(73) Assignee: UOP LLC, Des Plaines, IL (US)

(*) Notice: Subject to any disclaimer, the term of this patent is extended or adjusted under 35 U.S.C. 154(b) by 335 days.

(21) Appl. No.: 13/645,782

(22) Filed: Oct. 5, 2012

(65) Prior Publication Data

US 2014/0100406 A1    Apr. 10, 2014

(51) Int. Cl.

| | |
|---|---|
| *B01D 39/00* | (2006.01) |
| *B01D 39/14* | (2006.01) |
| *B01D 53/22* | (2006.01) |
| *B01D 53/12* | (2006.01) |
| *B01D 67/00* | (2006.01) |
| *B01D 61/00* | (2006.01) |
| *B01D 69/10* | (2006.01) |
| *B01D 69/14* | (2006.01) |
| *B01D 71/02* | (2006.01) |
| *B01D 71/62* | (2006.01) |

(52) U.S. Cl.
CPC .......... *B01D 61/007* (2013.01); *B01D 67/0088* (2013.01); *B01D 69/10* (2013.01); *B01D 69/141* (2013.01); *B01D 71/02* (2013.01); *B01D 71/024* (2013.01); *B01D 71/62* (2013.01); *B01D 2323/28* (2013.01)

(58) Field of Classification Search
CPC ........ B01D 39/00; B01D 67/00; B01D 63/00; B01D 53/228; B01D 67/0088; B01D 69/10; B01D 71/62; C08J 2375/04

USPC .......... 210/500.27, 490, 500.39, 640, 500.25; 264/41, 45.1; 427/244; 95/43, 45, 52, 95/50

See application file for complete search history.

(56) References Cited

U.S. PATENT DOCUMENTS

| | | | | |
|---|---|---|---|---|
| 4,217,404 A | * | 8/1980 | Verzwyvelt | 429/206 |
| 4,778,596 A | * | 10/1988 | Linder et al. | 210/638 |
| 4,806,189 A | * | 2/1989 | Kraus et al. | 156/155 |
| 4,919,694 A | * | 4/1990 | Hata et al. | 96/12 |
| 5,409,524 A | * | 4/1995 | Jensvold et al. | 96/8 |
| 8,132,678 B2 | * | 3/2012 | Liu et al. | 210/506 |
| 2005/0171395 A1 | * | 8/2005 | Huff et al. | 585/819 |
| 2008/0306318 A1 | * | 12/2008 | Ou et al. | 585/475 |
| 2010/0133190 A1 | * | 6/2010 | Liu et al. | 210/650 |
| 2010/0311565 A1 | | 12/2010 | Liu et al. | |

(Continued)

FOREIGN PATENT DOCUMENTS

| | | |
|---|---|---|
| RU | 2184106 C2 | 6/2002 |
| WO | 2011163293 A2 | 12/2011 |

(Continued)

OTHER PUBLICATIONS

International Search Report for PCT/US2013/060509, mailing date Jan. 16, 2014.

(Continued)

*Primary Examiner* — Ana Fortuna

(57) ABSTRACT

A separation membrane is described. The separation membrane comprises a porous inorganic membrane, the pores of the inorganic membrane being coated with a polybenzoxazole polymer coating. Methods of making the separation membrane and methods of separating xylenes using the separation membrane are also described.

20 Claims, 2 Drawing Sheets

(56) References Cited

U.S. PATENT DOCUMENTS

2011/0077312 A1* 3/2011 Liu et al. .................. 521/27
2011/0316181 A1* 12/2011 Liu et al. ................ 264/45.5
2012/0240763 A1* 9/2012 Liu et al. ..................... 95/45
2013/0118983 A1* 5/2013 Livingston et al. ....... 210/654
2013/0345481 A1* 12/2013 Ou et al. ................. 585/478
2014/0100406 A1* 4/2014 Liu et al. ................. 585/819

FOREIGN PATENT DOCUMENTS

WO    WO 2011163293 A1 * 12/2011

WO    WO 2012/010886 A1 *  1/2012

OTHER PUBLICATIONS

Deng et al., Isomorphously substituted B-MFI hollow fibre membranes for p-xylene separation from C8 aromatic mixtures, Separation and Purification Technology, 2011, pp. 323-329.

* cited by examiner

SEPARATION MEMBRANE

FIELD OF THE INVENTION

The present invention relates generally to separation membranes and more particularly to high temperature stable membranes, methods of making high temperature stable membranes, and methods of using high temperature stable membranes.

BACKGROUND OF THE INVENTION

When xylenes are subjected to isomerization, they form mixtures of para-xylene, ortho-xylene and meta-xylene. At the temperatures at which xylene isomerization is typically conducted, para-xylene forms approximately 24% of the equilibrium mixture, ortho-xylene about 23%, and meta-xylene about 53%. The C8 aromatic ethylbenzene is usually also present in a mixture of xylenes. Although each of these products has commercial value, the highest demand is for the para-xylene isomer.

Commercial processes for recovering para-xylene involve the selective removal of para-xylene by selective crystallization or sorption. One embodiment of a combined xylene separation process is illustrated in FIG. 1. The feed 5, having previously been stripped of all materials lighter than C8 aromatics, enters the C8 distillation column 10 and is separated into a stream 15 of C8 hydrocarbons and a stream 20 of C9+ hydrocarbons. The stream 15 of C8 hydrocarbons is sent to a sorption or crystallization zone 25 where it is separated into a stream 30 of highly pure para-xylene and a stream 35 containing ortho-xylene, meta-xylene, and ethyl benzene. Stream 35 is sent to an isomerization zone 40 where the xylenes are isomerized to an equilibrium xylene mixture, and some portion of any ethylbenzene present is either dealkylated (to benzene and ethylene) or converted to a xylene. Stream 45 which is a mixture of equilibrium xylenes and unconverted ethylbenzene is then recycled to the C8 distillation column 10.

The recycle loop typically contains separation operations (not shown) downstream of the isomerization zone, including, but not limited to, one or more of a toluene splitter to remove toluene and lighter hydrocarbons from the xylenes, and a xylene splitter to remove a portion of the o-xylene and heavier hydrocarbons from the C8 hydrocarbons as a separate product. In most commercial processes, other components are present in the recycle loop, such as saturates that boil in the C8 aromatic range or other components formed in the isomerization zone, such as hydrocarbons lighter than C8, hydrocarbons heavier than C8, and naphthenes.

It would be desirable to improve the separation of xylene isomers.

SUMMARY OF THE INVENTION

One aspect of the invention is a separation membrane. In one embodiment, the separation membrane comprises a porous inorganic membrane, the pores of the inorganic membrane being coated with a polybenzoxazole polymer coating.

Another aspect of the invention is a method of making a separation membrane. In one embodiment, the method comprises dissolving a polybenzoxazole precursor in a solvent to form a solution. A porous inorganic membrane is coated with the solution. The coated porous membrane is heated to form a polybenzoxazole polymer coated porous membrane.

Another aspect of the invention is a method of separating xylenes. In one embodiment, the method comprises contacting a vapor or liquid stream comprising para-xylene, and at least one of ortho-xylene, meta-xylene, and ethylbenzene with a porous inorganic membrane, the pores of the inorganic membrane being coated with a polybenzoxazole polymer coating, forming a membrane permeate stream enriched in para-xylene, ethylbenzene, or both, and a membrane retentate stream enriched in ortho-xylene, meta-xylene, or both.

DETAILED DESCRIPTION OF THE INVENTION

Figure 1:
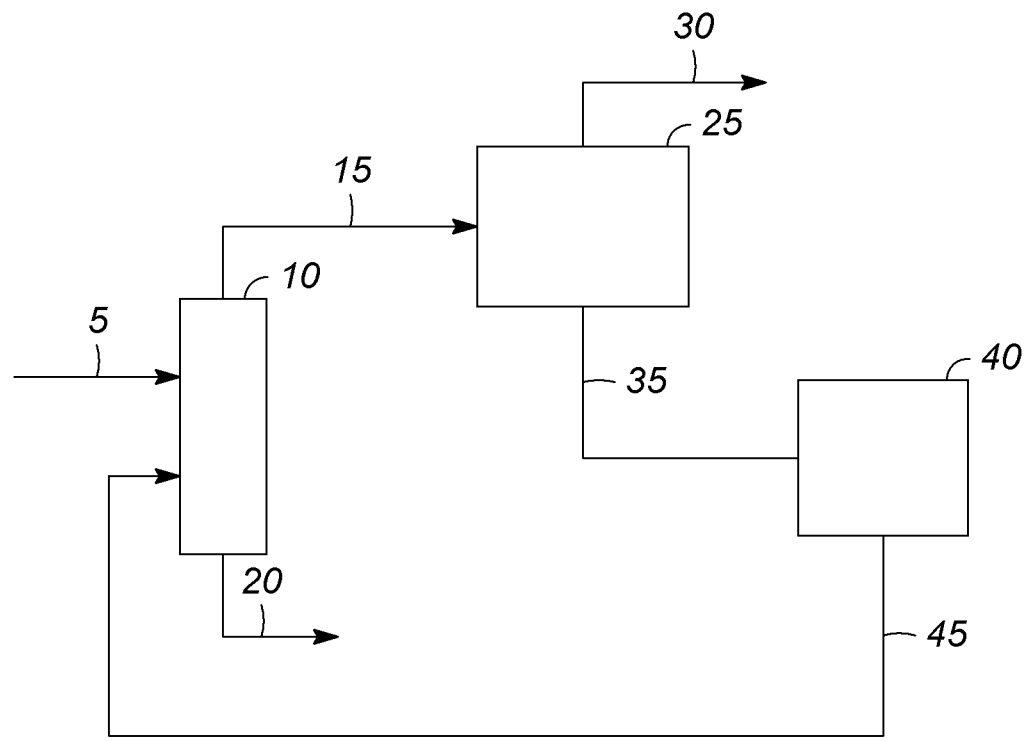
FIG. 1 is an illustration of a separation process including a crystallization or sorption zone and an isomerization zone.

The high temperature stable membranes can be used for xylene separation in xylene isomerization processes, and combined isomerization and crystallization or adsorptive separation processes. The high temperature stable membrane may be used in processing effluents from processes producing C8 aromatics including toluene disproportionation units, reforming units, C6 to C9 transalkylation units, and steam cracking units. The membranes are stable up to an operating temperature of about 500° C., are insoluble in organic solvents, and have a high flux (or permeance) for xylene separation.

The high temperature stable membrane is a porous inorganic membrane modified with a polybenzoxazole (PBO) polymer. The porous inorganic membrane incorporates a layer of PBO polymer on the inside wall of the pores of the separation surface. The PBO polymer enhances the membrane's selectivity compared to the unmodified porous inorganic membrane.

The inorganic membrane can be made of any suitable porous inorganic material, including, but not limited to, silica, metals such as stainless steel, alumina (including α-alumina, γ-alumina, and transition alumina), ceramics, molecular sieves, or combinations thereof. The selection of the material will depend on the conditions of the separation as well as the type of porous structure formed. The porous inorganic membranes can have different geometries, including, but not limited to, disks, tubes, hollow fiber, and the like.

The pore size is generally less than about 1000 nm, or less than about 500 nm, or less than about 400 nm, or less than about 300 nm, or less than about 200 nm, or less than about 100 nm, or less than about 50 nm, or in a range of about 0.5 nm to about 50 nm.

The PBO polymer can be derived from PBO precursors including, but not limited to, poly(hydroxyl imide), poly(hydroxyl amic acid), poly(hydroxyl amide), or mixtures thereof. The PBO precursors are soluble in solvents. Suitable solvents include, but are not limited to, organic solvents. Suitable organic solvents include, but are not limited to, 1-methyl-2-pyrrolidone, N,N-dimethylacetamide, N,N-dimethylformamide, 1,3-dioxolane, dichloromethane, or combinations thereof.

The porous inorganic membrane modified with a polybenzoxazole (PBO) polymer can be made using the following process. The porous inorganic membrane is cleaned and dried. One surface of the porous inorganic membrane is immersed in a PBO precursor solution for about 30 seconds to about 5 minutes. The excess solution on the surface of the porous inorganic membrane can be removed, and the surface carefully cleaned. The porous inorganic membrane with the PBO precursor can be dried at about room temperature under vacuum, followed by drying at about 100-300° C. under vacuum. The porous inorganic membrane can then be heated to about 350° C. to about 500° C., or about 400° C. to about 450° C. for 5 minutes to 2 hours to convert the PBO precursor polymer inside the pores of the porous inorganic membrane to form the high temperature stable PBO polymer.

The porous inorganic membrane modified with PBO can be used to enrich at least a portion of the recycle stream from an isomerization zone. The enriched stream, when combined with the remaining feed to a sorption or crystallization zone, will improve the efficiency of the selective sorption or crystallization zone because the feed will contain a higher concentration of para-xylene. Advantageously, the porous inorganic membrane modified with PBO can separate para-xylene and ethyl benzene from ortho-xylene and meta-xylene. The membrane permeate is enriched in para-xylene and ethyl benzene, and the residue or retentate is enriched in ortho-xylene and meta-xylene. By "enriched in para-xylene" it is meant that greater than about 50 wt %, or greater than about 60 wt %, or greater than about 70 wt %, or greater than about 80 wt %, or greater than about 90 wt %, or greater than about 95 wt % of the para-xylene present in the stream entering the porous inorganic membrane modified with PBO is recovered in the permeate stream. By "enriched in ortho-xylene and meta-xylene," it is meant that greater than about 50 wt %, or greater than about 60 wt %, or greater than about 70 wt %, or greater than about 80 wt %, or greater than about 90 wt %, or greater than about 95 wt % of the ortho-xylene and meta-xylene present in the stream entering the porous inorganic membrane modified with PBO is recovered in the retentate stream.

The membrane has high permeate flux. The selectivity for para-xylene and ethyl benzene over ortho-xylene and meta-xylene can be relatively low, while still providing a substantial process benefit because any material which can be sent back to the isomerization zone without going through the fractionation and separations zones reduces the capital and energy costs.

Although the entire xylene recycle stream can be subjected to the membrane separation, only a portion of the stream can be sent, if desired. In some embodiments, only about 10 to 50 percent by volume of the stream (preferably an aliquot portion) is sent to the membrane, with the remainder going to a xylene column for recycle to the selective para-xylene removal unit operation. The membrane separation is operated to recover at least about 50 wt %, at least about 60 wt %, at least about 70 wt %, or at least about 75 wt %, or at least about 80 wt %, or at least about 85 wt %, or at least about 90 wt %, or at least about 95 wt % of the para-xylene in the slip stream. Thus, the increase in the feed to the isomerization zone, as well as the downstream unit operations such as strippers and deheptanizers, as a result of the retentate being combined with the effluent from the para-xylene recovery unit operation is minimized.

Figure 2:
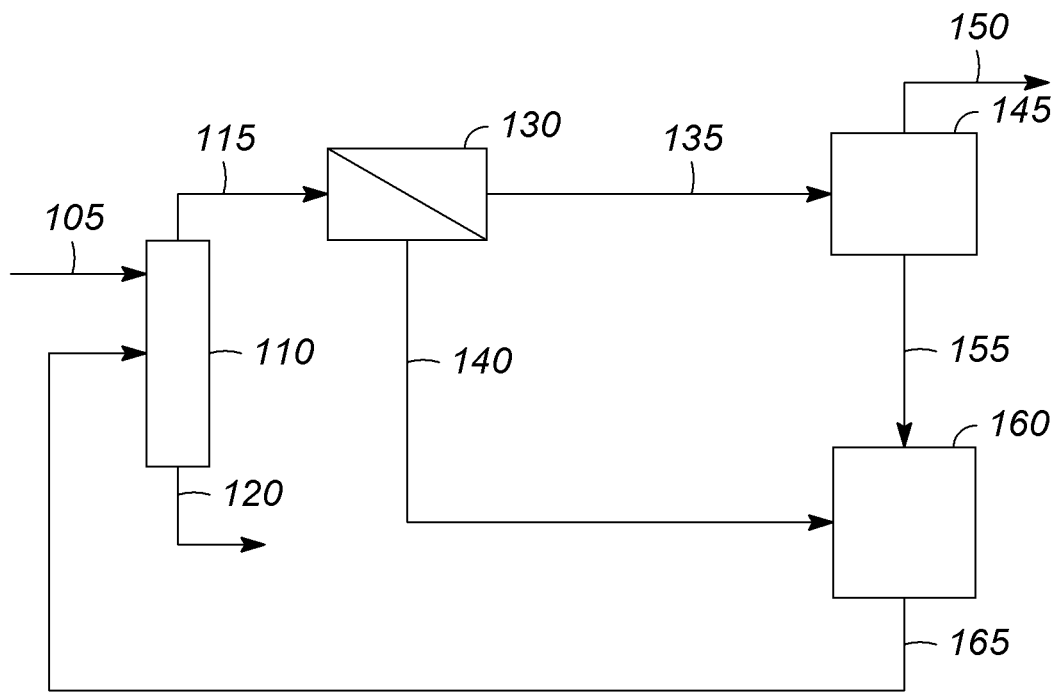
FIG. 2 is an illustration of one embodiment of a process using the porous inorganic membrane modified with a polybenzoxazole polymer.

In one embodiment, the porous inorganic membrane modified with PBO can be used in a combined isomerization and sorption or crystallization process, as illustrated in FIG. 2. A feed stream 105 enters the C8 distillation column 110 where it is separated into a stream 115 of C8 hydrocarbons and a stream 120 of C9+hydrocarbons. Stream 120 can be further processed, if desired. The stream 115 of C8 hydrocarbons is sent to the membrane separation zone 130. In the membrane separation zone 130, stream 115 is separated by the porous inorganic membrane modified with PBO into permeate stream 135 enriched in para-xylene and ethyl benzene, and retentate stream 140 enriched in ortho-xylene and meta-xylene.

In a typical process, the permeate stream 135 contains about 97 wt % of the para-xylene (about 97 wt % recovery) from stream 115, and about 95 wt % of the ethyl benzene (about 95 wt % recovery) from stream 115. Retentate stream 140 contains about 94 wt % of the ortho-xylene and about 94 wt % of the meta-xylene from stream 115.

Para-xylene enriched stream 135 can then be sent to a sorption or crystallization zone 145 where it is separated into stream 150, which is highly pure para-xylene (e.g., about 99.7%), and stream 155, which contains ethyl benzene and some ortho- and meta-xylene.

Stream 155 is sent to isomerization zone 160 where it is isomerized to produce an equilibrium mixture of xylene isomers. Some conversion of ethylbenzene either to benzene and ethylene or to xylene is also accomplished in the isomerization zone. Retentate stream 140 can also be sent to the isomerization zone, if desired. Stream 165, which is an equilibrium mixture of xylene isomers and unconverted ethylbenzene, can be recycled back to the C8 distillation column 110.

Because of the separation that takes place in the membrane separation zone 130, the sorption or crystallization zone 145 can be smaller than the sorption or crystallization zone 25 in the process shown in FIG. 1.

Figure 3:
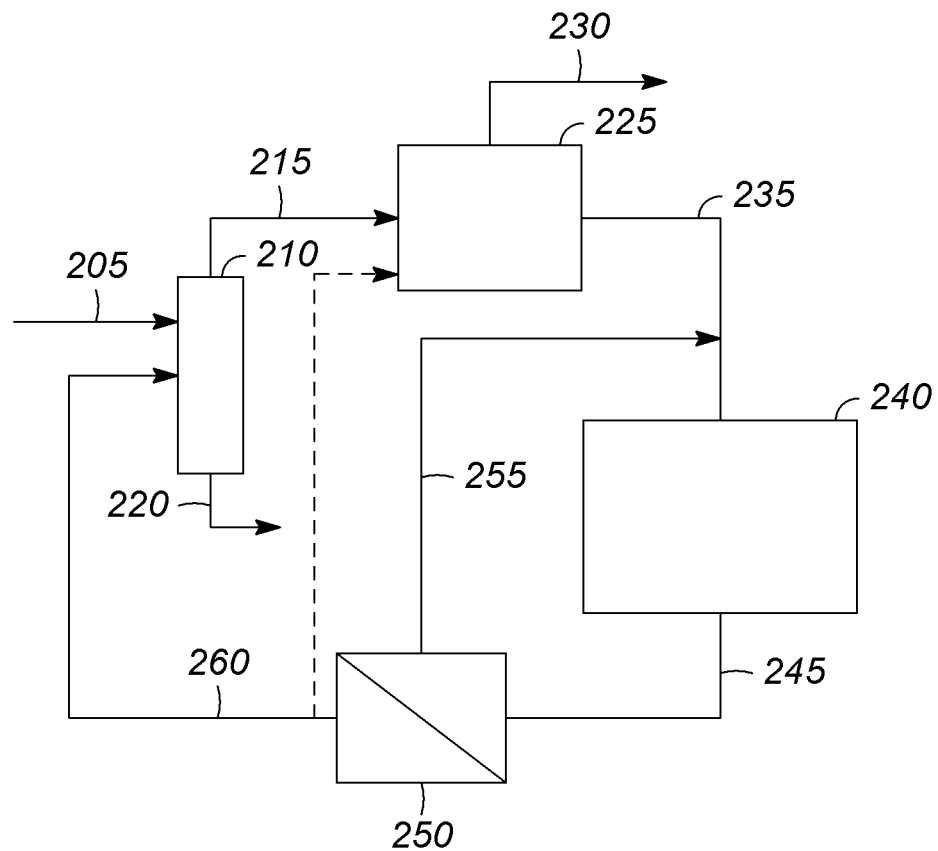
FIG. 3 is an illustration of another embodiment of a process using the porous inorganic membrane modified with a polybenzoxazole polymer.

FIG. 3 illustrates another embodiment of a process incorporating the porous inorganic membrane modified with PBO. The feed 205 enters C8 distillation column 210 where it is separated into a stream 215 of C8 hydrocarbons and a stream 220 of C9+hydrocarbons. The stream 215 of C8 hydrocarbons is sent to the sorption or crystallization zone 225 where it is separated into a highly pure para-xylene product stream 230 and stream 235 containing ortho-xylene, meta-xylene, and ethyl benzene. Stream 235 is sent to an isomerization zone 240 where it is isomerized to produce a stream 245 of a mixture of xylenes. Stream 245 is sent to the membrane separation zone 250. In the membrane separation zone 250, stream 245 is separated by the porous inorganic membrane modified with PBO into permeate stream 260 and retentate stream 255. Retentate stream 255, which is enriched in m-xylene and o-xylene, is recycled to the isomerization zone 240. Permeate stream 260, which is enriched in p-xylene and ethylbenzene, is recycled to the C8 distillation column 210. In some embodiments, stream 260 may be sent directly to sorption or crystallization zone 225. In some embodiments, a slip stream from stream 255 may be sent to C8 distillation column 210 to prevent the build up of heavy components in the isomerization zone. Stream 255 returns m-xylene and o-xylene directly back to the isomerization zone without needing to pass through the C8 distillation column or the selective p-xylene extraction zone. As a result, these units can be smaller than the sorption or crystallization zone 25 in the process shown in FIG. 1.

Figure 4:
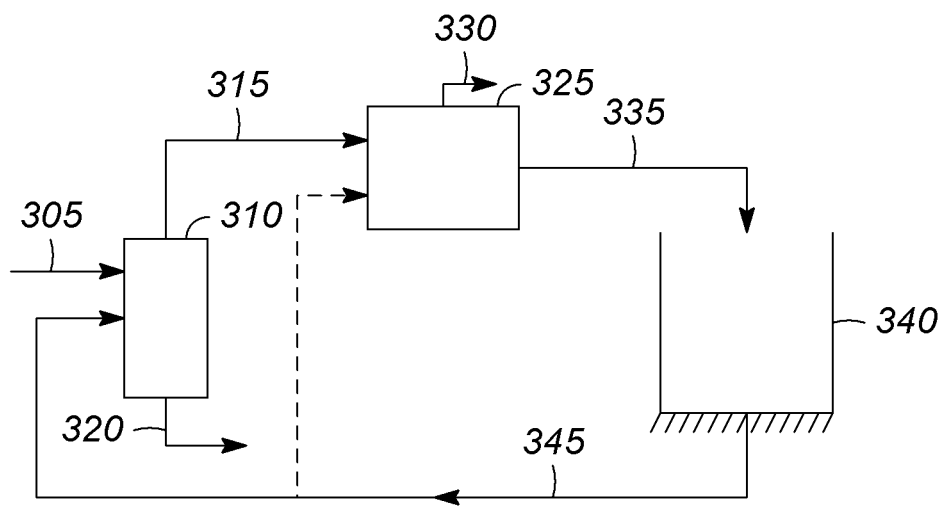
FIG. 4 is an illustration of still another embodiment of a process using the porous inorganic membrane modified with a polybenzoxazole polymer.

In the embodiment illustrated in FIG. 4, the feed 305 is sent to C8 distillation column 310 where it is separated into C8 stream 315 and C9+ stream 320. Stream 315 is sent to the sorption or crystallization zone 325 and separated into the highly pure para-xylene stream 330 and stream 335 containing ortho-xylene, meta-xylene, and ethyl benzene. Stream 335 is sent to a membrane reactor 340 in which the porous inorganic membrane coated with PBO forms a shell around the catalyst performing the isomerization. The PBO coated membrane is preferentially permeable to para-xylene and ethylbenzene. As the para-xylene and ethylbenzene are preferentially removed from the active area of the catalyst, the meta-xylene and ortho-xylene concentrations rise, allowing continued conversion of the meta-xylene and ortho-xylene to para-xylene. This higher conversion per pass of meta-xylene and ortho-xylene to para-xylene in the equilibrium limited xylene isomerization reaction reduces the recycle stream, allowing the C8 fractionation column 310 and sorption or crystallization zone 325 to be smaller than the analogous units in FIG. 1. Permeate stream 345 from the membrane reactor 340 is recycled to the C8 distillation column 310. In some embodiments, permeate stream 345 may be sent directly to sorption or crystallization zone 325. In some embodiments, a slip stream from the membrane reactor 340 may be sent to C8 distillation column 310 to prevent the build up of heavy components in the membrane reactor.

EXAMPLE

A porous ceramic membrane disk having a diameter of 39.0 mm, a thickness of 2.0 mm, and 180 nm pores (available from ECO Ceramics BV) was used.

The porous ceramic membrane disk was cleaned by rinsing with 2-propanol and water to remove surface impurities and dried at 110° C. for 24 hours in a vacuum oven. One surface of the porous ceramic membrane was immersed in a PBO precursor solution for 30 seconds. One PBO precursor solution was a solution of poly(hydroxyl imide) in 1-methyl-2-pyrrolidone, and another was poly(hydroxyl amic acid) in 1-methyl-2-pyrrolidone. The excess solution on the surface of the ceramic membrane was removed, and the surface was carefully cleaned. The ceramic membrane with the PBO precursor was dried at about room temperature under vacuum, followed by drying at about 200° C. under vacuum. The membrane was then heated to about 400° C. for 30 minutes to convert the PBO precursor polymer inside the pores of the ceramic membrane to form the high temperature stable PBO polymer.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed:

1. A separation membrane comprising:
 a porous inorganic membrane, the pores of the inorganic membrane being coated with a polybenzoxazole polymer coating, and wherein a polybenzoxazole layer is not formed on the porous inorganic membrane.

2. The separation membrane of claim 1, wherein the inorganic membrane comprises silica, alumina, ceramic, metal, molecular sieve, or combinations thereof.

3. The separation membrane of claim 1, wherein the pores of the inorganic membrane are less than about 1000 nm.

4. The separation membrane of claim 1, wherein the polybenzoxazole polymer is insoluble in organic solvent and is stable at a temperature of up to about 500° C.

5. A method of making a separation membrane comprising:
 dissolving a polybenzoxazole precursor in a solvent to form a solution;
 coating the porous inorganic membrane surface and its pores with the solution;
 removing the solution from the surface of the inorganic membrane; and
 heating the porous coated membrane to form a polybenzoxazole polymer coated membrane within the pores without a layer of the polybenzoxazole on the surface of the inorganic membrane.

6. The method of claim 5, wherein the polybenzoxazole precursor comprises poly(hydroxyl imide), poly(hydroxyl amic acid), poly(hydroxyl amide), or mixtures thereof.

7. The method of claim 5, wherein the solvent is an organic solvent.

8. The method of claim 5, wherein the solvent is 1-methyl-2-pyrrolidone, N,N-dimethylacetamide, N,N-dimethylformamide, 1,3-dioxolane, dichloromethane, or combinations thereof.

9. The method of claim 5, wherein the coated porous membrane is heated to a temperature in a range of about 350° C. to about 500° C.

10. The method of claim 5, wherein the inorganic membrane comprises silica, alumina, ceramic, metal, molecular sieves, or combinations thereof.

11. The method of claim 5, wherein the pores of the inorganic membrane are less than about 1000 nm.

12. A method of separating xylenes comprising:
 contacting a vapor or liquid stream comprising para-xylene, and at least one of ortho-xylene, meta-xylene, and ethyl benzene with a porous inorganic membrane, the pores of the inorganic membrane being coated with a polybenzoxazole polymer coating, while the surface of the membrane is not coated by the polybenzoxazole, forming a membrane permeate stream enriched in para-xylene, ethylbenzene, or both and a membrane retentate stream enriched in ortho-xylene, meta-xylene, or both.

13. The method of claim 12, wherein the inorganic membrane comprises silica, alumina, ceramic, metal, molecular sieve, or combinations thereof.

14. The method of claim 12, wherein the pores of the inorganic membrane are less than about 1000 nm.

15. The method of claim 12, wherein the stream comprising para-xylene and at least one of ortho-xylene, meta-xylene, and ethyl benzene is an overhead stream from a C8 distillation column, and wherein the permeate stream is introduced into a xylene adsorptive separation zone.

16. The method of claim 12, wherein the retentate is introduced into an isomerization zone.

17. The method of claim 12, wherein the stream comprising para-xylene and at least one of ortho-xylene, meta-xylene, and ethylbenzene is an effluent stream from an isomerization zone and wherein the permeate stream is introduced into a C8 distillation zone.

18. The method of claim 17, wherein the retentate is recycled to the isomerization zone.

19. The method of claim 12, wherein the stream comprising para-xylene and at least one of ortho-xylene, meta-xylene, and ethylbenzene is an overhead stream from a C8 distillation column, and wherein the permeate stream is introduced into a para-xylene selective crystallization separation zone.

20. The method of claim 19, wherein the retentate is introduced into an isomerization zone.

* * * * *